United States Patent [19]
Steinschneider

[11] Patent Number: 6,059,725
[45] Date of Patent: May 9, 2000

[54] PROLONGED APNEA RISK EVALUATION

[75] Inventor: Alfred Steinschneider, North Bethesda, Md.

[73] Assignee: American Sudden Infant Death Syndrome Institute, Marietta, Ga.

[21] Appl. No.: 09/129,566

[22] Filed: Aug. 5, 1998

Related U.S. Application Data

[60] Provisional application No. 60/054,785, Aug. 5, 1997.

[51] Int. Cl.$^7$ ....................................................... A61N 5/00
[52] U.S. Cl. .......................... 600/300; 600/590; 600/534
[58] Field of Search ..................................... 600/300–301, 600/479–483, 322–325, 481, 485, 500, 509, 527, 528, 529–542, 587, 590; 128/897–899, 903

[56] References Cited

U.S. PATENT DOCUMENTS

| | | | |
|---|---|---|---|
| 4,365,636 | 12/1982 | Barker | 128/716 |
| 4,597,394 | 7/1986 | Sackner | 128/777 |
| 4,838,275 | 6/1989 | Lee | 128/670 |
| 5,271,391 | 8/1998 | Graves | 128/207.18 |

OTHER PUBLICATIONS

Steinschneider, et al., "Identification of Risk for SIDS: Subsequent Siblings," Department of Health and Human Services (Grant Application: Apr., 1985).

Steinschneider, "Prolonged sleep apnea and respiratory instability: a discriminative study," *Pediatrics* 59 Suppl(6 Pt 2):962–70 (1977).

Steinschneider, et al., "The sudden infant death syndrome and apnea/obstruction during neonatal sleep and feeding," *Pediatrics* 70(6):858–63 (1982).

Weinstein, et al., "SIDS and prolonged apnea during sleep: Are they only a matter of State?," in *Sudden Infant Death Syndrome*, (Tilden, et al., eds.), pp. 413–421, Academic Press: New York, 1983.

Weinstein, et al., "The Effectiveness of Electronic Home Monitoring Programs in Preventing SIDS," in *Sudden Infant Death Syndrome*, (Tilden, et al., eds.), pp. 719–726, Academic Press: New York, 1983.

*Primary Examiner*—Cary O'Connor
*Assistant Examiner*—Michael Astorino
*Attorney, Agent, or Firm*—Arnall Golden & Gregory, LLP

[57] ABSTRACT

A method for determining the probability of an episode of prolonged apnea in an infant less than or equal to 6 months of age has been developed. The method includes conducting a physiological feeding study wherein the subject is bottle fed while monitoring respiration, heart rate, $O_2$ saturation, and sucking pressure, conducting a sleep study wherein the subject is allowed to sleep naturally while monitoring respiration, heart rate, $O_2$ saturation, and brain activity, and analyzing the data to make a prediction of the probability of a prolonged episode of sleep apnea. The method can further include correlating the results of the physiological feeding study and the sleep study with age, epidemiologic characteristics, and birth age. In the preferred embodiment, the sleep study is conducted in an environmentally controlled test chamber at 90°±2° F., and both respiratory effort and air flow are measured.

12 Claims, No Drawings

PROLONGED APNEA RISK EVALUATION

This appln claims benefit of provisional application Ser. No. 60/054,785 Aug. 5, 1997.

BACKGROUND OF THE INVENTION

What has been published:

A. Postmortem studies (microscopic and biochemical) have demonstrated that infants who die of SIDS, as a group, have a chronic abnormality which involves the brain stem.

B. Neonatal observations on subsequent SIDS victims (compared to controls) revealed group differences in reflexes, feeding behavior, unusual cries and an increased amount of brief apneic pauses during feeding and sleep.

C. A number of literature reviews have concluded that there is sufficient evidence to draw the general conclusion that, as a group, infants who die of SIDS have a subtle chronic abnormality that existed within the first few days of life.

D. Postmortem studies have demonstrated that respiratory failure or respiratory difficulty heralds the terminal event.

E. Postmortem studies have demonstrated that, as a group, SIDS victims had a number of apneic episodes prior to the terminal event.

F. Infants resuscitated following an apparent life threatening event (an episode of apnea or respiratory difficulty that was frightening to a parent) are at increased risk to die of SIDS.

G. Reviewers have concluded that there was no scientifically valid method for identifying infants at risk for SIDS or prolonged apnea.

H. Multi-channel recordings during sleep have become a standard in diagnosing sleep disorder and sleep apnea in adults.

I. In a published study (1978), infants who had prolonged apnea also had an increased frequency and duration of brief apneic pauses (statistically significant) when studied during sleep in a manner similar to that described in "How to test." It was during this study that the PSA4 and A6/D measures were developed.

J. A study demonstrated that 50% of infants who died of SIDS (N=10) had abnormal test scores (PSA4 or A6/D %) during a sleep or feeding evaluation conducted within the first week of life. These results were statistically significant.

K. In a prospective study supported by a research grant from the National Institute of Child Health and Human Development, a large number of normal infants born at the University of Maryland Hospital (Baltimore, Md.) were studied within the first and fourth week of life using most of the techniques described earlier. These data provided the basis, in part, for developing statistical norms. A newly developed apnea/bradycardia monitor (with an attached recorder) was made available for use by those whose sleep study was abnormal. Although the sample size was not totally adequate, a pilot study was conducted in which the SIDS rate was determined for those babies born at the University of Maryland Hospital prior to and during the conduct of the primary project and compared to comparable data for babies born at Johns Hopkins Hospital. The hypotheses examined were that: a) home monitoring and early resuscitative intervention will reduce the incidence of SIDS and b) the physiologic studies will identify infants at high risk. The results obtained were consistent with these hypotheses.

It is an object of the present invention to provide an improved method for predicting the liklihood an infant will be a risk for prolonged apnea.

SUMMARY OF THE INVENTION

A method for determining the probability of an episode of prolonged apnea in an infant less than or equal to 6 months of age has been developed. The method includes the following steps:

(a) conducting a physiological feeding study wherein the subject is bottle fed while monitoring respiration, heart rate, $O_2$ saturation, and sucking pressure, (b) conducting a sleep study wherein the subject is allowed to sleep naturally while monitoring respiration, heart rate, $O_2$ saturation, and brain activity, and (c) analyzing the data to make a prediction of the probability of a prolonged episode of sleep apnea. The method can further include correlating the results of the physiological feeding study and the sleep study with age, epidemiologic characteristics, and birth age. In the preferred embodiment, the sleep study is conducted in an environmentally controlled test chamber at 90°±2° F. and both respiratory effort and air flow are measured. In a further embodiment, an EKG is performed on the infants. Analysis includes determining A2/D %, the summed duration of apneic pauses $\geq 2$ sec divided by the duration of sleep times 100; determining the PSA4, where PSA4=$-2.695+0.607$ (MT)+0.023 (AR)+0.042 (AN) $-0.143$ (A2/D %), where:

MT is mean duration of apnea in total sleep

AR is % of REM epochs during which apnea $\geq 2$ sec was initiated and

NR is % of NREM epochs during which apnea $\geq 2$ sec was initiated; determining the A6/D %, where A6/D % is summed duration of apneic pauses $\geq 6$ sec divided by the duration of sleep times 100;

determining the longest airway obstruction (MO) episode (REM, NREM, Total); determining the MO2%, where MO2%: percentage of airway obstruction episodes ($\geq 2$ sec) initiated within REM epochs, NREM epochs, and Total sleep; determining MO2/D %, where MO2/D % is the summed duration of airway obstruction episodes $\geq 2$ sec divided by the duration of sleep times 100; determining MO6%, where MO6% is the percentage of airway obstruction episodes ($\geq 6$ sec) initiated within REM epochs, NREM epochs, and Total sleep; and determining MO6/D %, where MO6/D % equals the summed duration of airway obstruction episodes $\geq 6$ sec divided by the duration of sleep times 100.

DETAILED DESCRIPTION OF THE INVENTION

Who to test:

A. Infants, $\leq 6$ months of age, at increased risk for SIDS based on epidemiologic characteristics.

B. Infants, $\leq 6$ months of age, for whom there is concern because of prolonged apnea or SIDS.

How to test:

A. Infants to be observed in an environmentally controlled (quiet, ambient temperature 90°±2° F.) test room.

B. Physiologic feeding study

1) Measures a) Respiration:Chest (eg, mercury strain gauge positioned across lower thorax), b) Respiration:Nasal (eg, tape thermistor below nostril), c) EKG/heart rate (eg, tape flat disc surface electrodes to mid-sternum and mid-posterior thorax), d) pulse $O_2$ saturation (eg, tape pulse oximeter to foot), e) sucking pressure (eg, insert sterile catheter through base of nipple and into milk bottle; catheter to be attached to pressure transducer).

2) Procedure:

Infant to be bottle fed (burped as needed) until satisfied while recording all of the above biologic activities (Respiration:Chest, Respiration:Nasal, ECG, heart rate, pulse changes, peripheral $O_2$ saturation, sucking). Physiologic feeding study to be done prior to sleep study and while hungry. If not successful, feeding study should be done after sleep study.

C. Sleep (Nap) Study

1) Measures a) Respiration:Chest (eg, mercury strain gauge positioned across lower thorax), b) Respiration:Nasal (eg, tape thermistor below nostril), c) EKG/heart rate (eg, tape flat disc surface electrodes to mid-sternum and mid-posterior thorax), d) pulse $O_2$ saturation (eg, tape pulse oximeter to foot), e) EEG (eg, tape flat disc surface electrodes to C3-A2 and C4-A1), f) EOG (eg, tape flat disc surface electrodes to the outer canthi bilaterally and nasion).

2) Procedure: Above physiological activity to be recorded continuously throughout entire natural sleep period. Sleep onset and end of sleep to be determined visually. Observer also records the occurrence of gross motor activity. One hour of sleep time, excluding time of gross motor activity, is the minimum acceptable sleep period.

How to analyze:

A. Physiologic Feeding Study

1) All sucking bursts $\geq 5.0$ sec in duration are identified and measured to an accuracy of 0.1 sec. A sucking burst is defined as a series of sucks with an interval between successive sucks of <2.0 sec. Sucking bursts <5.0 sec long are rejected from further analysis.

2) All periods of apnea or a decrease in amplitude of the respiration:nasal signal by at least 80% (AO) of $\geq 2$ sec in duration beginning within a sucking burst are measured to an accuracy of 0.1 sec.

3) Statistical measures derived from these basic data include: longest burst duration, mean burst duration, longest AO, AO/D % (the total sum of AO duration per 100 sec of sucking time), and AO Density (the number of AO episodes per 100 sec of sucking time).

4) An AO measure is defined as "Abnormal" if it is in the upper 5th percentile of the normative values (corrected for postnatal age).

B. Sleep (Nap) Study

1) The sleep period is divided into 15-sec successive epochs and each epoch characterized as either a REM epoch or NREM epoch based on the occurrence of rapid eye movements (detected primarily from an examination of the EOG recordings).

2) An epoch is excluded from further analysis if it includes at least 5 sec of movement artifact.

3) Central apnea is detected as the cessation of respiratory activity in both respiration:nasal and respiration:chest sensors. All periods of central apnea >2 sec in duration are measured to a tenth of a sec. Duration is measured from the end of a respiratory cycle to the beginning of the next respiratory cycle.

4) Periods ($\geq 2$ sec in duration) of airway obstruction (MO) are identified as REM activity in the respiration:nasal sensor occurring in conjunction with respiratory activity in the respiration:chest sensor. These periods are measured to a tenth of a sec.

5) All periods of $O_2$ desaturation $\leq 85\%$ are identified and durations measured to a tenth of a sec.

6) EKG is examined for gross evidence of a cardiac arrhythmia or prolonged QT interval.

7) A number of statistical measures are derived and compared to age corrected norms. Those observed measures in the upper 5th percentile of the normative population are considered "Abnormal." These statistical measures include:

a) longest apnea (REM, NREM, Total)

b) mean duration apnea (REM, NREM, Total)

c) percentage of apneic pauses ($\geq 2$ sec) initiated within REM epochs, NREM epochs, and Total Sleep d) percentage of sleep time involved in periodic apnea ($\geq 22$ sec)

e) A2/D %: Summed duration of apneic pauses $\geq 2$ sec divided by the duration of sleep times 100 f) PSA4: PSA4=−2.695+0.607 (MT)+0.023 (AR)+0.042 (AN)−0.143 (A2/D %)

where:

MT is mean duration of apnea in total sleep

AR is % of REM epochs during which apnea $\geq 2$ sec was initiated

NR is % of NREM epochs during which apnea $\geq 2$ sec was initiated.

g) percentage of apneic pauses ($\geq 6$ sec) initiated within REM epochs, NREM epochs, and total sleep h) percentage of sleep time involved in periodic apnea ($\geq 6$ sec)

i) A6/D %: Summed duration of apneic pauses $\geq 6$ sec divided by the duration of sleep times 100 j) longest airway obstruction (MO) episode (REM, NREM, Total)

k) MO2%: percentage of airway obstruction episodes ($\geq 2$ sec) initiated within REM epochs, NREM epochs, and Total sleep l) MO2/D %: Summed duration of airway obstruction episodes $\geq 2$ sec divided by the duration of sleep times 100 m) MO6%: percentage of airway obstruction episodes ($\geq 6$ sec) initiated within REM epochs, NREM epochs, and Total sleep n) MO6/D %: Summed duration of airway obstruction episodes $\geq 6$ sec divided by the duration of sleep times 100

How to interpret analysis:

A. Asymptomatic infants and infants who had an apparent life threatening event: An abnormal PSA4 or A6/D % or AO/D % increases the risk for prolonged apnea 5–6 times greater than that of infants with normal scores.

B. Small premature infants: An equation was developed based on a logistic regression analysis which revealed that infants whose overall score is abnormal will be at 12–13 times greater risk to develop prolonged apnea than infants whose score is within normal limits. This equation includes the A6/D and MO2/D % measures along with information on the infant's sex, method of feeding, race, gestational age, postnatal age, and whether the infant has gastroesophageal reflux disease or being treated with a respiratory stimulant. Information regarding maternal smoking and the number of prior pregnancies are also included in this equation.

Premie PSA=3.55+0.90 (SEX)+0.37 (FEED)+0.92

(RESPSTIM)+1.95 (RACE)+0.62 (PRIMIGRAV)+0.30

(REFLUX)−1.09 (MO2/D %)+0.53 (A6/D %)+0.50

(SMPACK)−0.03 (AGE)−0.30 (GESTAGE)−2.59

(REFLUX*PRIMIGRAV)−2.69 (REFLUX*FEED)+2.74

(Reflux*MO2/D %). Normal Premie PSA score: $\leq 0.1754$

What to do with interpretation:
A. This evaluation provides objective information that will assist a physician in deciding whether to recommend home monitoring.
B. This evaluation provides objective information to be used medically in deciding when to discontinue home monitoring.
C. This evaluation provides objective information to be used in deciding when to employ a respiratory stimulant and when to discontinue this form of treatment.
D. An abnormal physiologic feeding study will confirm the clinical impression of dysphagia and the need for further diagnostic evaluation or medical intervention.
E. The detection of a cardiac arrhythmia or prolonged QT interval could result in a more in-depth cardiac evaluation and possible treatments.

How to do all above in the best way:
A. Studies should be conducted in an environmentally controlled test chamber.
B. Ambient temperature should be maintained at 90°±2° F.
C. Studies should be conducted by persons skilled in the conduct of such studies and in working with infants.
D. Studies should be initiated when the infant is hungry.
E. Physiologic recordings should include both respiratory effort and air flow.
F. Recordings should include measures of respiratory difficulty (eg, $O_2$ saturation, heart rate).
G. EKG should be obtained as a means of evaluating the validity of the heart rate recordings and for to detect a possible cardiac arrhythmia.
H. Need an objective means of determining the beginning and end of sucking bursts.
I. Need an objective means of determining the occurrence of rapid eye movements during sleep.
J. Apnea duration should be measured as the interval between the end of a respiratory cycle and the beginning of the next cycle.
K. Data extraction from the two studies should be done by persons skilled in this activity.
L. Interpretation of statistical measures should include not only summary measures but also the individual components. This can best be done by persons (eg, MD) skilled in the interpretation of such data.

The following procedures should be avoided:
A. Studies conducted under uncontrolled environmental conditions (noise level, ambient temperature).
B. Studies conducted by persons poorly trained in the conduct of these studies.
C. The use of techniques that alters respiratory activity (eg, simultaneous use of an esophageal probe to measure pH).
D. Failure to provide an objective measure of the beginning and end of a sucking burst.
E. Failure to adequately define the beginning and end of sleep.
F. Failure to measure both respiratory effort and airflow and to differentiate between central apnea and airway obstruction episodes.
G. Use of different criteria for measuring the duration of apnea.
H. Failure to obtain an objective measure of rapid eye movements.
I. Use of different criteria for defining REM and NREM epochs.
J. Use of different criteria for defining the duration of an epoch (eg, 10 sec, 30 sec, 60 sec).
K. Use of different statistical measures.
L. Use of different criteria for determining if a study is abnormal.
M. Use of relative risk statements for inappropriate measures and/or for statistical measures obtained under non-standardized conditions.

Supporting data:
A. The initial set of normative data for both the apnea measures during sleep and all measures during feeding were obtained from 128 infants, born at the Upstate Medical Center (Syracuse, N.Y.). Each infant was studied initially within the first week of age and then on four separate occasions over 180 day period. The norms for the first four weeks of life were replaced by data obtained from over 570 term infants born at the University of Maryland Hospital. These latter studies were conducted under a research project supported by a grant from the National Institute of Child Health and Human Development.
B. Supported by a research grant from the Department of Health and Human Services (Bureau of Maternal and Child Health and Resources Development), a prospective study was conducted, in part, to evaluate the effectiveness of neonatal measures of respiratory instability obtained during feeding and sleep in identifying the infant at risk for prolonged apnea. Data were obtained from 154 infants (siblings of a SIDS victim) tested within the first and fourth week of life. All infants, regardless of test scores, were followed at home on an apnea/bradycardia monitor with event recording capability. The results provided support for the hypothesis and demonstrated that infants with an abnormal PSA4 or A6/D % or AO/D % when studied within the first week of life were at increased risk to develop prolonged apnea. These results were statistically significant. Abnormal test results in the first week of life identified 71% of infants who developed prolonged apnea. Furthermore, infants who had abnormal test results were at 6.9 times greater risk for developing apnea.
C. The most recent study involved 810 infants, all of whom had been referred to the Institute at less than six months of age for home monitoring. All were tested (Sleep and Physiologic Feeding Studies) and, regardless of the laboratory results, followed at home on an apnea/bradycardia monitor with event recording capabilities. For the purpose of statistical analyses, infants were placed into one of two groups. One group consisted of infants (Asymptomatic/ALTE Group, N=526) who were referred because: a) of an apparent life threatening event, b) a sibling died of SIDS, c) a sibling was on a monitor, or d) parental anxiety. Twenty-four percent of these infants had an abnormal evaluation (abnormal PSA4 or A6/D % or AO/D %) and accounted for 62 percent of the infants who had an episode of prolonged apnea. Infants who had an abnormal evaluation were at 5.2 times greater risk to develop prolonged apnea when compared to infants who had a normal evaluation. The second group (Premie Apnea Group, N=284) consisted of infants born prematurely who had episodes of apnea or bradycardia while in the neonatal intensive care unit. Through the use of an equation derived from a logistic regression analysis (see Footnote 2, which included measures from the sleep study, it was possible to identify (abnormal evaluation) 23% of these infants who had 78% of the episodes of prolonged apnea. Infants within the Premie Apnea Group who had an abnormal evaluation had a 12.3 times greater risk to develop prolonged apnea when compared to those infants within this group whose evaluation was normal.

I claim:

1. A method for determining a probability of an episode of prolonged apnea in an infant subject less than or equal to 6 months of age comprising:

(a) conducting a physiological feeding study wherein the subject is bottle fed while monitoring respiration, heart rate, $O_2$ saturation, and sucking pressure, and (b) conducting a sleep study wherein the subject is allowed to sleep naturally while monitoring respiration, heart rate, $O_2$ saturation, and brain activity, (c) correlating results of the physiological feeding study and the sleep study with age, epidemiologic characteristics, and birth age, and, (d) analyzing correlated data from the physiolozical feeding study and the sleep study to make a determination of the probability of a prolonged episode of sleep apnea.

2. The method of claim 1 wherein the sleep study is conducted in an environmentally controlled test chamber at $90°±2°$ F.

3. The method of claim 1 further comprising measuring both respiratory effort and air flow.

4. The method of claim 1 further comprising making an EKG.

5. The method of claim 1 comprising determining A2/D %, wherein A2/D % is the summed duration of apneic pauses greater than or equal to 2 sec divided by the duration of sleep times 100.

6. The method of claim 1 further comprising determining the PSA4, where PSA4=−2.695+0.607 (MT)+0.023(AR)+0.042 (AN)−0.143 (A2/D %), where:

MT is mean duration of apnea in total sleep

AR is % of REM epochs during which apnea $\geq 2$ sec was initiated,

AN is % of NREM epochs during which apnea $\geq 2$ sec was initiated, and

A2/D % is the summed duration of apneic pauses greater than or equal to 2 sec divided by the duration of sleep times 100.

7. The method of claim 1 further comprising determining A6/D %, where A6/D % is summed duration of apneic pauses greater than or equal to six sec divided by the duration of sleep times 100.

8. The method of claim 1 further comprising determining a longest airway obstruction (MO) episode (REM, NREM, Total).

9. The method of claim 1 further comprising determining MO2%, wherein MO2% is percentage of airway obstruction episodes greater than or equal to two sec initiated within REM epochs, NREM epochs, and Total sleep.

10. The method of claim 1 further comprising determining MO2/D %, where MO2/D % is the summed duration of airway obstruction episodes $\geq 2$ sec divided by the duration of sleep times 100.

11. The method of claim 1 further comprising determining MO6%, where MO6% is the percentage of airway obstruction episodes ($\geq 6$ sec) initiated within REM epochs, NREM epochs, and Total sleep.

12. The method of claim 1 further comprising determining MO6/D %, where MO6/D % equals the summed duration of airway obstruction episodes $\geq 6$ sec divided by the duration of sleep times 100.

* * * * *